(12) United States Patent
Lim

(10) Patent No.: US 9,724,222 B2
(45) Date of Patent: Aug. 8, 2017

(54) RESHEATHABLE STENT DELIVERY SYSTEM

(75) Inventor: Chhuon Lim, Santa Ana, CA (US)

(73) Assignee: Covidien LP, Mansfield, MA (US)

( * ) Notice: Subject to any disclaimer, the term of this patent is extended or adjusted under 35 U.S.C. 154(b) by 142 days.

(21) Appl. No.: 13/553,855

(22) Filed: Jul. 20, 2012

(65) Prior Publication Data

US 2014/0025150 A1 Jan. 23, 2014

(51) Int. Cl.
*A61F 2/966* (2013.01)
*A61F 2/95* (2013.01)

(52) U.S. Cl.
CPC ...... *A61F 2/966* (2013.01); *A61F 2002/9505* (2013.01); *A61F 2002/9534* (2013.01); *A61F 2002/9665* (2013.01)

(58) Field of Classification Search
CPC .............. A61F 2/95; A61F 2002/9505; A61F 2002/9511; A61F 2002/9534; A61F 2002/9583; A61F 2002/9665; A61F 2002/9522; A61F 2002/011; A61F 2/958; A61F 2/962; A61F 2/966; A61F 2/97; A61F 2/2427; A61F 2/2436; A61B 2017/1205
USPC ......................................... 623/1.11; 606/198
See application file for complete search history.

(56) References Cited

U.S. PATENT DOCUMENTS

| | | |
|---|---|---|
| 4,655,771 A | 4/1987 | Wallsten |
| 4,723,936 A | 2/1988 | Buchbinder et al. |
| 4,877,031 A | 10/1989 | Conway et al. |
| 4,990,151 A | 2/1991 | Wallsten |
| 5,026,377 A | 6/1991 | Burton et al. |
| 5,147,370 A | 9/1992 | McNamara et al. |
| 5,318,529 A | 6/1994 | Kontos |
| 5,445,646 A | 8/1995 | Euteneuer et al. |
| 5,474,563 A | 12/1995 | Myler et al. |
| 5,484,444 A | 1/1996 | Braunschweiler et al. |
| 5,545,209 A * | 8/1996 | Roberts ................... A61F 2/958 604/103.05 |
| 5,571,135 A | 11/1996 | Fraser et al. |
| 5,636,641 A | 6/1997 | Fariabi |
| 5,695,499 A | 12/1997 | Helgerson et al. |
| 5,702,418 A | 12/1997 | Ravenscroft |
| 5,709,703 A | 1/1998 | Lukic et al. |

(Continued)

FOREIGN PATENT DOCUMENTS

| | | |
|---|---|---|
| CN | 102159157 | 8/2011 |
| EP | 775470 A1 | 5/1997 |

(Continued)

OTHER PUBLICATIONS

Covidien's Pipeline Embolization Device and Delivery System Product Description and Instructions for Use, Jun. 2010.

*Primary Examiner* — Tuan V Nguyen
*Assistant Examiner* — Chima Igboko
(74) *Attorney, Agent, or Firm* — Mark Kertz

(57) ABSTRACT

The present disclosure relates generally to medical implant devices for use within a patient's body and, more particularly, relates to systems and methods for resheathing vascular devices. In some embodiments, a stent delivery system includes a stent expandable from a compressed configuration to an expanded configuration. The stent has a proximal end and a distal end and an anchoring element having a proximal portion and a distal portion, wherein the anchoring element engages the stent in the expanded configuration.

17 Claims, 13 Drawing Sheets

(56) References Cited

U.S. PATENT DOCUMENTS

| | | | |
|---|---|---|---|
| 5,725,571 A * | 3/1998 | Imbert et al. | 623/1.11 |
| 5,776,141 A * | 7/1998 | Klein et al. | 623/1.11 |
| 5,824,041 A * | 10/1998 | Lenker et al. | 606/195 |
| 5,935,161 A | 8/1999 | Robinson et al. | |
| 5,968,053 A | 10/1999 | Revelas | |
| 6,077,295 A | 6/2000 | Limon et al. | |
| 6,077,297 A | 6/2000 | Robinson et al. | |
| 6,123,723 A | 9/2000 | Konya et al. | |
| 6,126,685 A | 10/2000 | Lenker et al. | |
| 6,149,680 A | 11/2000 | Shelso et al. | |
| 6,152,944 A | 11/2000 | Holman et al. | |
| 6,193,739 B1 | 2/2001 | Chevillon et al. | |
| 6,251,132 B1 | 6/2001 | Ravenscroft et al. | |
| 6,264,683 B1 | 7/2001 | Stack et al. | |
| 6,287,315 B1 | 9/2001 | Wijeratne et al. | |
| 6,350,278 B1 | 2/2002 | Lenker et al. | |
| 6,371,953 B1 | 4/2002 | Beyar et al. | |
| 6,383,171 B1 | 5/2002 | Gifford et al. | |
| 6,387,118 B1 * | 5/2002 | Hanson | 623/1.11 |
| 6,395,008 B1 | 5/2002 | Ellis | |
| 6,395,017 B1 | 5/2002 | Dwyer et al. | |
| 6,419,693 B1 | 7/2002 | Fariabi | |
| 6,425,898 B1 | 7/2002 | Wilson et al. | |
| 6,428,552 B1 | 8/2002 | Sparks | |
| 6,443,971 B1 | 9/2002 | Boylan et al. | |
| 6,468,298 B1 | 10/2002 | Pelton | |
| 6,517,547 B1 | 2/2003 | Feeser et al. | |
| 6,562,063 B1 | 5/2003 | Euteneuer et al. | |
| 6,576,006 B2 | 6/2003 | Limon et al. | |
| 6,582,460 B1 | 6/2003 | Cryer | |
| 6,602,271 B2 | 8/2003 | Adams et al. | |
| 6,607,551 B1 | 8/2003 | Sullivan et al. | |
| 6,669,719 B2 | 12/2003 | Wallace et al. | |
| 6,699,274 B2 | 3/2004 | Stinson | |
| 6,706,055 B2 | 3/2004 | Douk et al. | |
| 6,764,504 B2 | 7/2004 | Wang et al. | |
| 6,808,529 B2 | 10/2004 | Fulkerson | |
| 6,815,325 B2 | 11/2004 | Ishii | |
| 6,830,575 B2 | 12/2004 | Stenzel et al. | |
| 6,843,802 B1 | 1/2005 | Villalobos et al. | |
| 6,866,679 B2 | 3/2005 | Kusleika | |
| 6,932,837 B2 | 8/2005 | Amplatz et al. | |
| 6,960,227 B2 | 11/2005 | Jones et al. | |
| 6,989,024 B2 | 1/2006 | Hebert et al. | |
| 7,001,422 B2 | 2/2006 | Escamilla et al. | |
| 7,011,675 B2 | 3/2006 | Hemerick et al. | |
| 7,074,236 B2 | 7/2006 | Rabkin et al. | |
| 7,147,656 B2 | 12/2006 | Andreas et al. | |
| 7,306,624 B2 | 12/2007 | Yodfat et al. | |
| 7,357,812 B2 | 4/2008 | Andreas et al. | |
| 7,371,248 B2 | 5/2008 | Dapolito et al. | |
| 7,427,288 B2 | 9/2008 | Sater | |
| 7,473,271 B2 | 1/2009 | Gunderson | |
| 7,473,272 B2 | 1/2009 | Pryor | |
| 7,572,290 B2 | 8/2009 | Yodfat et al. | |
| 7,651,520 B2 | 1/2010 | Fischell et al. | |
| 7,655,031 B2 | 2/2010 | Tenne et al. | |
| 7,691,138 B2 * | 4/2010 | Stenzel et al. | 623/1.11 |
| 7,717,953 B2 | 5/2010 | Kaplan et al. | |
| 7,758,624 B2 | 7/2010 | Dorn et al. | |
| 7,867,267 B2 | 1/2011 | Sullivan et al. | |
| 7,942,925 B2 | 5/2011 | Yodfat et al. | |
| 7,955,370 B2 | 6/2011 | Gunderson | |
| 7,981,148 B2 | 7/2011 | Aguilar et al. | |
| 7,993,385 B2 | 8/2011 | Levine et al. | |
| 8,025,692 B2 | 9/2011 | Feeser | |
| 8,034,095 B2 | 10/2011 | Randolph et al. | |
| 8,042,720 B2 | 10/2011 | Shifrin et al. | |
| 8,066,754 B2 | 11/2011 | Malewicz | |
| 8,083,791 B2 | 12/2011 | Kaplan et al. | |
| 8,092,508 B2 | 1/2012 | Leynov et al. | |
| 8,109,987 B2 | 2/2012 | Kaplan et al. | |
| 8,133,266 B2 | 3/2012 | Thomas et al. | |
| 8,147,534 B2 | 4/2012 | Berez et al. | |
| 8,187,314 B2 | 5/2012 | Davis et al. | |
| 8,257,432 B2 | 9/2012 | Kaplan et al. | |
| 8,298,276 B2 | 10/2012 | Ozawa et al. | |
| 8,317,850 B2 | 11/2012 | Kusleika | |
| 8,366,763 B2 | 2/2013 | Davis et al. | |
| 8,382,818 B2 | 2/2013 | Davis et al. | |
| 8,790,387 B2 * | 7/2014 | Nguyen et al. | 623/1.11 |
| 9,072,624 B2 | 7/2015 | Brown | |
| 2001/0020173 A1 | 9/2001 | Klumb et al. | |
| 2001/0044591 A1 | 11/2001 | Stevens et al. | |
| 2001/0049547 A1 | 12/2001 | Moore | |
| 2002/0029046 A1 | 3/2002 | Lorentzen Cornelius et al. | |
| 2002/0049412 A1 | 4/2002 | Madrid et al. | |
| 2002/0072789 A1 * | 6/2002 | Hackett et al. | 623/1.12 |
| 2002/0107526 A1 | 8/2002 | Greenberg et al. | |
| 2002/0111666 A1 | 8/2002 | Hart et al. | |
| 2002/0138128 A1 * | 9/2002 | Stiger et al. | 623/1.11 |
| 2003/0004539 A1 | 1/2003 | Linder et al. | |
| 2003/0009208 A1 | 1/2003 | Snyder et al. | |
| 2003/0050600 A1 | 3/2003 | Ressemann et al. | |
| 2003/0212410 A1 | 11/2003 | Stenzel et al. | |
| 2003/0212430 A1 | 11/2003 | Bose et al. | |
| 2004/0024416 A1 | 2/2004 | Yodfat et al. | |
| 2004/0111095 A1 | 6/2004 | Gordon et al. | |
| 2004/0220585 A1 * | 11/2004 | Nikolchev | 606/108 |
| 2004/0230285 A1 | 11/2004 | Gifford et al. | |
| 2004/0260384 A1 | 12/2004 | Allen | |
| 2005/0096724 A1 * | 5/2005 | Stenzel et al. | 623/1.11 |
| 2005/0119719 A1 | 6/2005 | Wallace et al. | |
| 2005/0125051 A1 | 6/2005 | Eidenschink et al. | |
| 2005/0131449 A1 | 6/2005 | Salahieh et al. | |
| 2005/0143773 A1 | 6/2005 | Abrams et al. | |
| 2005/0182475 A1 | 8/2005 | Jen et al. | |
| 2005/0240254 A1 | 10/2005 | Austin | |
| 2005/0273149 A1 | 12/2005 | Tran et al. | |
| 2006/0036309 A1 | 2/2006 | Hebert et al. | |
| 2006/0058865 A1 | 3/2006 | Case et al. | |
| 2006/0074477 A1 | 4/2006 | Berthiaume et al. | |
| 2006/0116750 A1 | 6/2006 | Hebert et al. | |
| 2006/0184226 A1 * | 8/2006 | Austin | 623/1.11 |
| 2006/0212042 A1 | 9/2006 | Lamport et al. | |
| 2006/0235502 A1 | 10/2006 | Belluche et al. | |
| 2007/0027520 A1 * | 2/2007 | Sherburne | 623/1.11 |
| 2007/0043430 A1 * | 2/2007 | Stinson | 623/1.15 |
| 2007/0078504 A1 * | 4/2007 | Mialhe | 623/1.11 |
| 2007/0088323 A1 | 4/2007 | Campbell et al. | |
| 2007/0100421 A1 | 5/2007 | Griffin | |
| 2007/0117645 A1 | 5/2007 | Nakashima | |
| 2007/0203563 A1 | 8/2007 | Hebert et al. | |
| 2007/0239254 A1 * | 10/2007 | Chia et al. | 623/1.11 |
| 2007/0239261 A1 | 10/2007 | Bose et al. | |
| 2007/0255388 A1 | 11/2007 | Rudakov et al. | |
| 2007/0299500 A1 | 12/2007 | Hebert et al. | |
| 2007/0299501 A1 | 12/2007 | Hebert et al. | |
| 2007/0299502 A1 | 12/2007 | Hebert et al. | |
| 2008/0009934 A1 | 1/2008 | Schneider et al. | |
| 2008/0015678 A1 | 1/2008 | Kaplan et al. | |
| 2008/0027528 A1 | 1/2008 | Jagger et al. | |
| 2008/0033528 A1 | 2/2008 | Satasiya et al. | |
| 2008/0051705 A1 | 2/2008 | Von Oepen et al. | |
| 2008/0071301 A1 | 3/2008 | Matsuura et al. | |
| 2008/0077229 A1 * | 3/2008 | Andreas | A61F 2/95 623/1.11 |
| 2008/0140180 A1 | 6/2008 | Dolan et al. | |
| 2008/0147162 A1 | 6/2008 | Andreas et al. | |
| 2008/0188865 A1 | 8/2008 | Miller et al. | |
| 2008/0234795 A1 * | 9/2008 | Snow et al. | 623/1.11 |
| 2008/0243225 A1 | 10/2008 | Satasiya et al. | |
| 2008/0255653 A1 * | 10/2008 | Schkolnik | A61F 2/95 623/1.11 |
| 2008/0255654 A1 | 10/2008 | Hebert et al. | |
| 2008/0300667 A1 * | 12/2008 | Hebert et al. | 623/1.11 |
| 2009/0082069 A1 * | 3/2009 | Condado | 600/4 |
| 2009/0105802 A1 * | 4/2009 | Henry et al. | 623/1.11 |
| 2009/0125053 A1 | 5/2009 | Ferrera et al. | |
| 2009/0132019 A1 * | 5/2009 | Duffy et al. | 623/1.11 |
| 2009/0138066 A1 | 5/2009 | Leopold et al. | |
| 2009/0143849 A1 | 6/2009 | Ozawa et al. | |
| 2009/0157048 A1 | 6/2009 | Sutermeister et al. | |
| 2009/0204196 A1 * | 8/2009 | Weber | 623/1.2 |

(56) References Cited

U.S. PATENT DOCUMENTS

| | | |
|---|---|---|
| 2009/0264985 A1 | 10/2009 | Bruszewski |
| 2009/0287292 A1* | 11/2009 | Becking .................. A61F 2/95 |
| | | 623/1.11 |
| 2009/0299449 A1* | 12/2009 | Styrc .......................... 623/1.11 |
| 2009/0318947 A1* | 12/2009 | Garcia et al. ................ 606/191 |
| 2010/0049293 A1 | 2/2010 | Zukowski et al. |
| 2010/0049297 A1* | 2/2010 | Dorn ........................... 623/1.11 |
| 2010/0057184 A1 | 3/2010 | Randolph et al. |
| 2010/0057185 A1* | 3/2010 | Melsheimer et al. ....... 623/1.12 |
| 2010/0069852 A1 | 3/2010 | Kelley |
| 2010/0087913 A1 | 4/2010 | Rabkin et al. |
| 2010/0094394 A1 | 4/2010 | Beach et al. |
| 2010/0100106 A1 | 4/2010 | Ferrera |
| 2010/0198334 A1 | 8/2010 | Yodfat et al. |
| 2010/0204770 A1 | 8/2010 | Mas et al. |
| 2010/0262157 A1* | 10/2010 | Silver et al. ................. 606/108 |
| 2010/0268328 A1* | 10/2010 | Stiger .......................... 623/1.23 |
| 2010/0274270 A1 | 10/2010 | Patel et al. |
| 2010/0298931 A1* | 11/2010 | Quadri et al. ............... 623/2.11 |
| 2010/0331951 A1* | 12/2010 | Bei et al. ..................... 623/1.11 |
| 2011/0009943 A1* | 1/2011 | Paul et al. ................... 623/1.11 |
| 2011/0022157 A1 | 1/2011 | Essinger et al. |
| 2011/0029065 A1 | 2/2011 | Wood et al. |
| 2011/0034987 A1 | 2/2011 | Kennedy |
| 2011/0054586 A1* | 3/2011 | Mayberry et al. ........... 623/1.11 |
| 2011/0093055 A1* | 4/2011 | Kujawski ..................... 623/1.11 |
| 2011/0098804 A1 | 4/2011 | Yeung et al. |
| 2011/0106235 A1 | 5/2011 | Haverkost et al. |
| 2011/0112623 A1* | 5/2011 | Schatz ......................... 623/1.11 |
| 2011/0152760 A1 | 6/2011 | Parker |
| 2011/0160763 A1 | 6/2011 | Ferrera et al. |
| 2011/0178588 A1 | 7/2011 | Haselby |
| 2011/0190862 A1 | 8/2011 | Bashiri et al. |
| 2011/0190865 A1 | 8/2011 | McHugo et al. |
| 2011/0208292 A1 | 8/2011 | Von Oepen et al. |
| 2011/0276129 A1* | 11/2011 | Salahieh ............... A61F 2/2418 |
| | | 623/2.18 |
| 2011/0288626 A1 | 11/2011 | Straubinger et al. |
| 2011/0319904 A1 | 12/2011 | Hollett et al. |
| 2012/0029607 A1 | 2/2012 | McHugo et al. |
| 2012/0035700 A1 | 2/2012 | Leanna et al. |
| 2012/0053681 A1 | 3/2012 | Alkhatib et al. |
| 2012/0059449 A1 | 3/2012 | Dorn et al. |
| 2012/0065660 A1 | 3/2012 | Ferrera et al. |
| 2012/0116494 A1 | 5/2012 | Leynov et al. |
| 2012/0253447 A1 | 10/2012 | Hayasaka et al. |
| 2012/0316638 A1 | 12/2012 | Grad et al. |
| 2013/0085562 A1 | 4/2013 | Rincon et al. |
| 2013/0131775 A1 | 5/2013 | Hadley et al. |
| 2013/0172925 A1 | 7/2013 | Garcia et al. |
| 2013/0172979 A1 | 7/2013 | Fargahi |
| 2013/0226276 A1 | 8/2013 | Newell et al. |
| 2013/0226278 A1 | 8/2013 | Newell et al. |
| 2013/0261730 A1 | 10/2013 | Bose et al. |
| 2013/0274618 A1 | 10/2013 | Hou et al. |
| 2013/0274859 A1 | 10/2013 | Argentine |
| 2013/0304185 A1 | 11/2013 | Newell et al. |
| 2014/0031918 A1 | 1/2014 | Newell et al. |
| 2014/0148893 A1 | 5/2014 | Kusleika |
| 2014/0200648 A1 | 7/2014 | Newell et al. |
| 2015/0032198 A1 | 1/2015 | Folk |
| 2015/0066129 A1 | 3/2015 | Nageswaran et al. |
| 2015/0066130 A1 | 3/2015 | Haggstrom et al. |
| 2015/0066131 A1 | 3/2015 | Luong et al. |

FOREIGN PATENT DOCUMENTS

| | | |
|---|---|---|
| EP | 1637176 A1 | 3/2006 |
| EP | 1656963 A1 | 5/2006 |
| EP | 2 078 512 | 7/2009 |
| GB | 2179258 A | 3/1987 |
| WO | WO-96/01591 | 1/1996 |
| WO | WO-01/49212 | 7/2001 |
| WO | WO-01/89619 | 11/2001 |
| WO | WO-2007/095031 A2 | 8/2007 |
| WO | WO-2007/117645 A2 | 10/2007 |
| WO | WO-2010/027485 | 3/2010 |
| WO | WO-2010/086320 | 8/2010 |
| WO | WO-2010/123831 | 10/2010 |
| WO | WO-2010/127838 A2 | 11/2010 |
| WO | WO-2011/014814 A2 | 2/2011 |
| WO | WO-2011/076408 | 6/2011 |
| WO | WO-2011/095966 | 8/2011 |
| WO | WO-2011/144351 A2 | 11/2011 |
| WO | WO-2012/040240 | 3/2012 |
| WO | WO-2012/158152 A1 | 11/2012 |

* cited by examiner

RESHEATHABLE STENT DELIVERY SYSTEM

BACKGROUND

Lumens in the body can change in size, shape, and/or patency, and such changes can present complications or affect associated body functions. For example, the walls of the vasculature, particularly arterial walls, may develop pathological dilatation called an aneurysm. Aneurysms are observed as a ballooning-out of the wall of an artery. This is a result of the vessel wall being weakened by disease, injury or a congenital abnormality. Aneurysms have thin, weak walls and have a tendency to rupture and are often caused or made worse by high blood pressure. Aneurysms can be found in different parts of the body; the most common being abdominal aortic aneurysms (AAA) and the brain or cerebral aneurysms. The mere presence of an aneurysm is not always life-threatening, but they can have serious heath consequences such as a stroke if one should rupture in the brain. Additionally, a ruptured aneurysm can also result in death.

Vascular devices or "occluding devices" such as stents are often used to treat patients with aneurysms. Stent and/or other occluding devices can be implanted within the vasculature of a patient by a delivery system such as a catheter. Precise and accurate positioning of these vascular devices at a target site is often required before a stent can be safely and effectively detached from the stent delivery system to a target site within a patient's vasculature. Positioning can be a delicate process that may require positioning and re-positioning of the stent delivery device prior to the detachment of the stent.

SUMMARY

The efficacy of the occluding device can depend greatly on the precise and accurate positioning of the occluding device within a patient's vessel. At least one aspect of the disclosure provides devices and methods for implanting an occluding device or devices (e.g., stent or stents) in the body. The occluding device can direct the blood flow within a vessel away from an aneurysm. Such an occluding device can allow adequate blood flow to be provided to adjacent structures such that those structures, whether they are branch vessels or oxygen demanding tissues, are not deprived of the necessary blood flow.

At least one aspect of the disclosure provides occluding device delivery systems and methods for positioning an occluding device or devices in the body. Such occluding delivery systems may resheath a partially deployed occluding device so that the occluding device may be re-positioned and/or re-deployed.

Some embodiments provide a stent delivery system comprising: a deployable stent expandable from a compressed configuration to an expanded configuration, the stent having a proximal end portion and a distal end portion; an outer anchoring element having a proximal portion and a distal portion, the distal portion comprising a divide along a longitudinal length thereof, wherein the outer element engages an outer surface of the proximal end portion in the expanded configuration, and the distal portion of the outer element is configured to deflect radially outward by the stent when the stent expands; and a delivery member configured to encapsulate at least partially the stent and the outer anchoring element prior to expanding the stent. Optionally, the stent delivery system may further include a capping element configured to cover at least partially the distal end of the stent.

In some embodiments, the outer anchoring element frictionally engages the stent in the at least partially expanded configuration. In certain embodiments, the outer anchoring element expands as the stent expands. In certain embodiments, the expanded anchoring element tapers from the distal end to the proximal end. In certain embodiments, the outer anchoring element has a slit along its axial length. In certain embodiments, the outer anchoring element encapsulates at least partially the stent.

Some embodiments provide a stent delivery system comprising: a stent expandable from a compressed configuration to an expanded configuration and having a proximal end portion, a distal end portion, and an inner lumen; an outer anchoring element configured to engage a partially expanded stent, the outer anchoring element having a proximal portion and a distal portion, the distal portion being configured to flare radially outward when the stent is expanded; an inner anchoring element expandable from a compressed configuration to an expanded configuration and being disposed in the stent and configured to engage the inner surface of the stent; and an elongate tube disposed radially within the outer anchoring element, the elongate tube configured to at least partially encapsulate the inner anchoring element. Optionally, the stent delivery system may further include an inner anchoring element expandable from a compressed state to an expanded state, wherein at least a portion of the inner anchoring element is disposed inside the stent and configured to engage the inner wall of the stent in the expanded state.

Optionally, the method of deploying a stent at a target site may further include retracting the partially deployed stent by causing a relative proximal motion of the elongate member. Optionally, the method may further include re-deploying the retracted stent at the target site.

In some embodiments, the target site is an aneurysm or a branch vessel. Additional features and advantages of the subject technology will be set forth in the description below, and in part will be apparent from the description, or may be learned by practice of the subject technology. The advantages of the subject technology will be realized and attained by the structure particularly pointed out in the written description and claims hereof as well as the appended drawings.

Some embodiments provide a method of positioning a stent at a target site comprising: advancing distally a distal end of a self-expanding stent relative to a catheter, whereby, when unrestrained, the distal end of the stent radially expands from within a capping element attached to a wire, the stent being positioned between an inner anchoring element, radially within the stent, and an outer anchoring element, radially outward of the stent and axially offset from the inner anchoring element; and advancing the wire distally, whereby the inner anchoring element (i) flares radially outward, (ii) engages an inner surface of the stent in an expanded configuration, and (iii) moves a proximal end of the stent distally away from an outer anchoring element.

Some embodiments provide a method of positioning a stent at a target site comprising: advancing distally a distal end of a self-expanding stent relative to a catheter, whereby, when unrestrained, the distal end of the stent radially expands from within a capping element attached to a wire, the stent being positioned between an inner anchoring element, radially within the stent, and an outer anchoring element, radially outward of the stent and axially offset from the inner anchoring element; retracting the wire proximally, whereby the inner anchoring element moves proximally relative to the stent without engaging the stent and becomes axially aligned with the outer anchoring element, whereby the proximal end of the stent is frictionally engaged with the outer anchoring element at an outer surface and with the inner anchoring element at an inner surface; and retracting the stent proximally relative to the catheter, whereby the stent is entirely resheathed within the catheter It is to be understood that both the foregoing general description and the following detailed description are exemplary and explanatory and are intended to provide further explanation of the subject technology as claimed.

BRIEF DESCRIPTION OF THE DRAWINGS

The accompanying drawings, which are included to provide further understanding of the subject technology and are incorporated in and constitute a part of this specification, illustrate aspects of the subject technology and together with the description serve to explain the principles of the subject technology.

DETAILED DESCRIPTION

In the following detailed description, numerous specific details are set forth to provide a full understanding of the subject technology. It will be apparent, however, to one ordinarily skilled in the art that the subject technology may be practiced without some of these specific details. In other instances, well-known structures and techniques have not been shown in detail so as not to obscure the subject technology.

While the preferred embodiments of the subject technology relate to stent delivery systems and means of deploying and implanting a stent device in a vasculature to treat aneurysms, the systems and methods of this disclosure may generally be used for or in conjunction with any implantable device to treat any disorder that is compatible with one or more embodiments as described herein. Suitable examples of implantable devices include, but are not limited to, stents, dilation balloons, embolic coils, embolic protection device, and the like.

Figure 1:
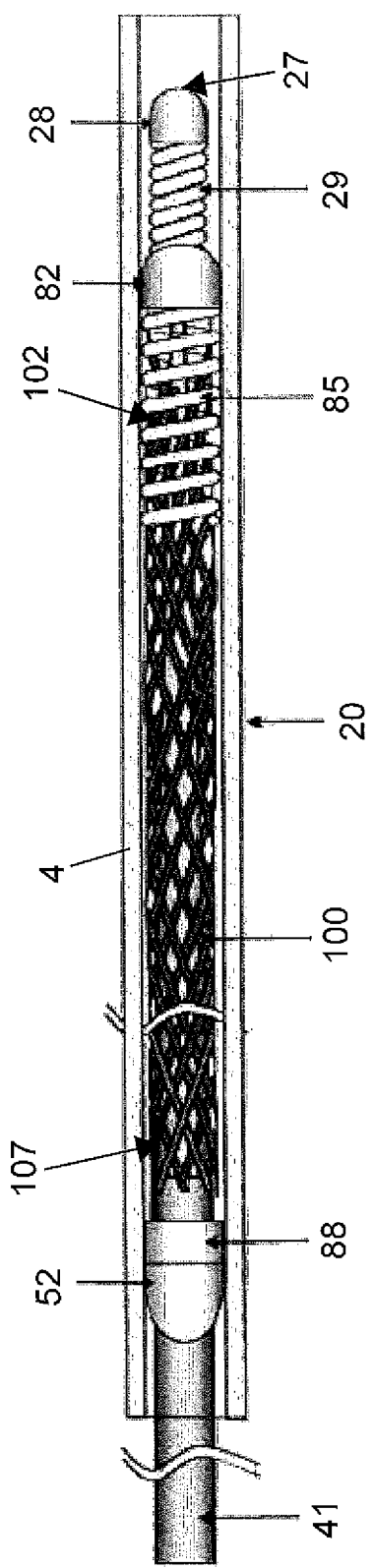
FIG. 1 is a partial cross-sectional view of an exemplary stent delivery system, according to one or more embodiments disclosed.

Described herein are various embodiments of stent delivery systems exhibiting small cross-sections which are highly flexible. Referring to FIG. 1, illustrated is an exemplary stent delivery system 20 including a stent 100 carried by a core wire 41 as arranged within an introducer sheath or catheter 4. The stent 100 and the core wire 41 may be cooperatively movable within the catheter 4 in order to deliver the stent 100 to a predetermined treatment site, such as an aneurysm, within the vasculature of a patient. Accordingly, the catheter 4 may be configured to be introduced and advanced through the vasculature of the patient. The catheter 4 may be made from various thermoplastics, e.g., PTFE, FEP, HDPE, PEEK, etc., which may optionally be lined on the inner surface of the catheter 4 or an adjacent surface with a hydrophilic material such as PVP or some other plastic coating. Additionally, either surface may be coated with various combinations of different materials, depending upon the desired results.

The stent 100 may be characterized as a vascular occluding device and/or a embolization device, as generally known in the art. These terms are broad terms and are intended to have their ordinary meaning and include, unless expressly otherwise stated or incompatible with the description of, each of the stents and other vascular devices described herein. In some embodiments, the stent 100 may be a self-expanding stent made of two or more round or ovoid wire filaments. The filaments may be formed of known flexible materials including shape memory materials, such as nitinol, platinum and stainless steel. In some embodiments, the stent 100 is fabricated from platinum/8% tungsten and 35N LT (cobalt nickel alloy, which is a low titanium version of MP35N alloy) alloy wires. In other embodiments, one or more of the filaments can be formed of a biocompatible metal material or a biocompatible polymer.

The wire filaments may be braided into a resulting lattice-like structure. In at least one embodiment, during braiding or winding of the stent 100, the filaments may be loosely braided using a 1-over-2-under-2 system. In other embodiments, however, other methods of braiding may be followed, without departing from the scope of the disclosure. The stent 100 may exhibit a porosity configured to reduce haemodynamic flow into, for example, an aneurysm, but simultaneously allow perfusion to an adjacent branch vessel. As will be appreciated, the porosity of the stent 100 may be adjusted by "packing" the stent during deployment, as known in the art. The ends of the stent 100 may be cut to length and therefore remain free for radial expansion and contraction. The stent 100 may exhibit a high degree of flexibility due to the materials used, the density (i.e., the porosity) of the filaments, and the fact that the ends are not secured.

The flexibility of the core wire 41 allows the stent delivery system 20 to bend and conform to the curvature of the vasculature as needed for positional movement of the stent 100 within the vasculature. The core wire 41 may be made of a conventional guidewire material and have a solid cross-section. Alternatively, the core wire 41 can be formed from a hypotube. The material used for the core wire 41 can be any of the known guidewire materials including superelastic metals or shape memory alloys, e.g., nitinol. Alternatively, the core wire 41 can be formed of metals such as stainless steel.

[0035] In one or more embodiments, the stent delivery system 20 may exhibit the same degree of flexion along its entire length. In other embodiments, however, the stent delivery system 20 can have two or more longitudinal sections, each with differing degrees of flexion/stiffness. The different degrees of flexions for the stent delivery system 20 can be created using different materials and/or thicknesses within different longitudinal sections of the core wire 41. In another embodiment, the flexion of the core wire 41 can be controlled by spaced cuts (not shown) formed within the core wire 41. These cuts can be longitudinally and/or circumferentially spaced from each other.

A tip 28 and flexible tip coil 29 may be secured to the distal end 27 of the delivery core wire 41. The tip 28 can be characterized as a distal solder joint formed of a continuous end cap or cover as shown in the figures, which securely receives a distal end of the tip coil 29. Flexion control is provided to the distal end 27 of the delivery core wire 41 by the tip coil 29. However, in an embodiment, the tip 28 can be free of the coil 29. As illustrated, the tip 28 may have a non-percutaneous, atraumatic end face. The tip coil 29 may be configured to surround at least a portion of the core wire 41. The tip coil 29 is flexible so that it will conform to and follow the path of a vessel within the patient as the tip 28 is advanced along the vessel and the core wire 41 bends to follow the tortuous path of the vasculature.

At the proximal end 107 of the stent 100, a proximal solder joint 52 and proximal marker 88 prevent or limit lateral movement of the stent 100 along the length of the core wire 41 in the direction of the proximal end 107. As illustrated, the proximal end 107 of the stent 100 may be axially offset from the proximal marker 88 by a short distance. In other embodiments, however, the stent 100 may shift axially during introduction into the vasculature of the patient and contact the proximal marker 88 which prevents or limits the stent 100 from moving along the length of the core wire 41 away from a distally located protective coil 85 coupled to an adjacent or mid solder joint 82.

After navigating the length of the catheter 4 to the predetermined treatment site within the patient, the stent 100 may be deployed from the catheter 4 in a variety of ways. In one embodiment, the catheter 4 is retracted while maintaining the position of the core wire 41 to expose the distal end 27 of the delivery core wire 41 and the distal end 102 of the stent 100. Upon exiting the catheter 4, the portion of the stent 100 that is not situated between the protective coil 85 and the core wire 41 and that is not covered by the catheter 4 begins to expand radially. The catheter 4 may then be further retracted until enough of the stent 100 is exposed such that the expansion diameter of the stent 100 is sufficient to engage the walls of the vessel (not shown), such as a blood vessel. Upon engaging a portion of said vessel, the stent 100 may be at least partially anchored within the vessel.

The core wire 41 may then be rotated at its proximal end, which causes rotation at the distal end 27 relative to the stent 100. The rotation of the core wire 41 also causes twisting of the protective coil 85, which pushes the distal end 102 of the stent 100 out from beneath the protective coil 85 like a corkscrew. Once the distal end 102 of the stent 100 is released from the protective coil 85, it expands to engage the walls of the vessel. The catheter 4 may then be further retracted to expose and expand the remaining portions of the stent 100.

Those skilled in the art will readily recognize that variations of this deployment method are possible. For example, the catheter 4 may be further retracted before rotating the core wire 41, such as by expanding the proximal end 107 of the stent 100 before expanding the distal end 102. Other examples of deployment variations include causing or otherwise creating variable porosity of the stent 100.

Once the entire stent 100 is expanded, the core wire 41 may then be retracted back into the catheter 4 by pulling proximally on the core wire 41 and maintaining the catheter 4 in its position. The proximal taper of the solder joint 52 coupled to the proximal marker 88 helps guide retraction of the core wire 41 back into the catheter 4. The core wire 41 and the catheter 4 may then be both retracted from the vessel and vasculature of the patient.

Resheathable Stent Delivery System

Figure 2A:
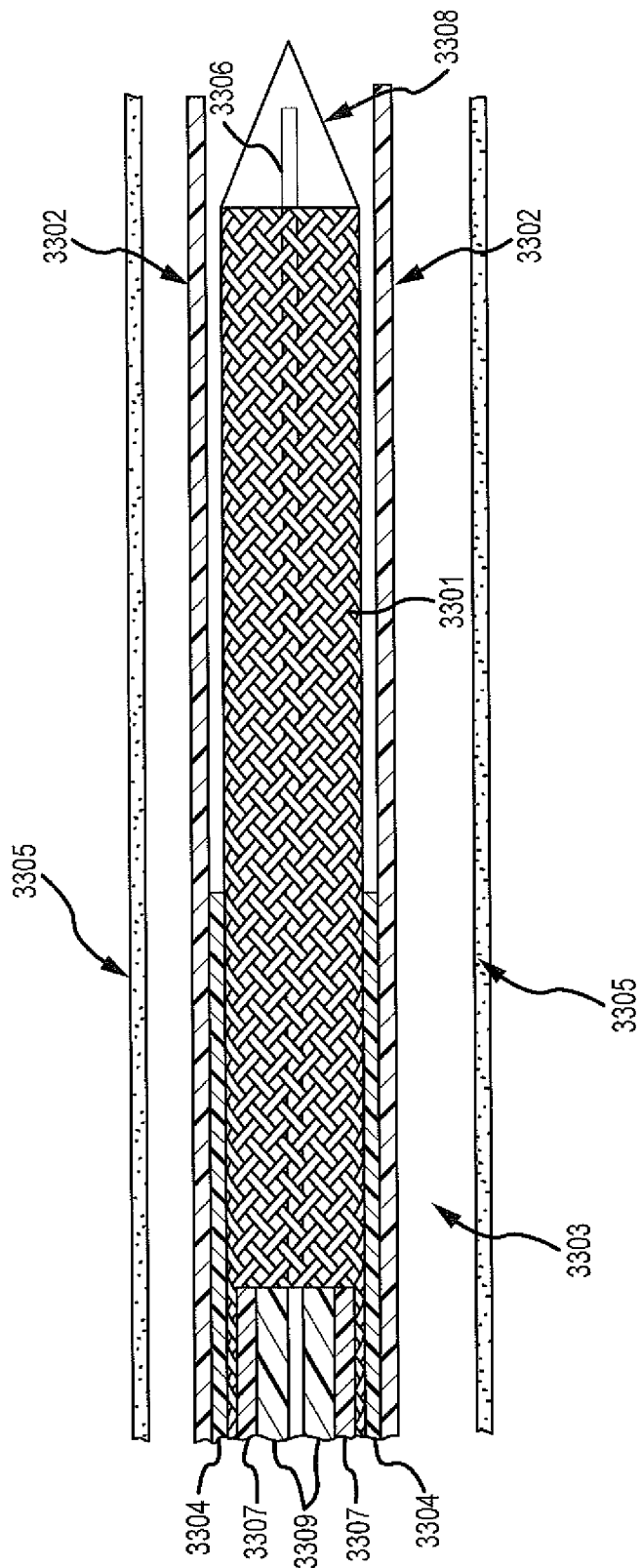
FIGS. 2A and 2B depict an embodiment of the resheathable stent delivery system.
Figure 2B:
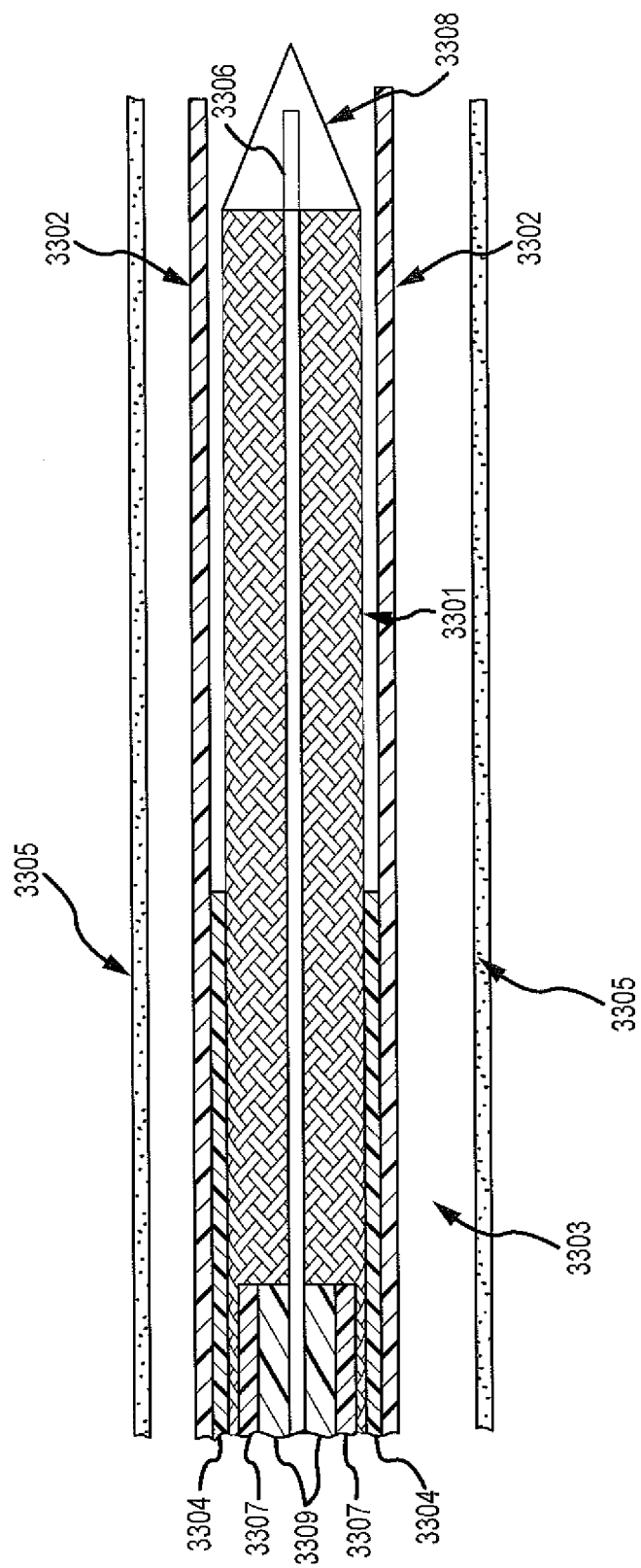

While at least some embodiments described herein relate to self-expandable stents, any suitable vascular device that is compatible with one or more embodiments may be used with and/or in conjunction with the subject technology. FIGS. 2A-2B show a resheathable stent delivery system 3300 in which a self-expandable stent 3301 is in a radially compressed state or, in other words, a state prior to the deployment of the self-expandable stent 3301 into the vasculature of a patient.

FIG. 2A and FIG. 2B show embodiments in which the self-expandable stent 3301 has been washed out in FIG. 2B in order to show certain details that may otherwise be obscured. As shown in FIGS. 2A-2B, a substantial portion of the self-expandable stent 3301 is disposed in the catheter 3302. More specifically, a substantial portion of the self-expandable stent 3301 is disposed at or near the distal portion 3303 of the catheter 3302. The catheter 3302 may act as an outer sheath which at least partially encapsulates the outer anchoring element 3304 which in turn at least partially encapsulates the self-expandable stent 3301.

As shown in FIGS. 2A-2B, at least a portion of the outer anchoring element 3304 is sandwiched between at least a portion of the catheter 3302 and at least a portion of the self-expandable stent 3301. The self-expandable stent 3301 is disposed over a guide wire 3306 which runs through the lumen defined by the expandable stent 3001 and through an elongate member, such as elongate tube 3307. The guide wire 3306 and the elongate tube 3307 both may be independently controlled to move proximally and distally relative to each other. In some embodiments, the proximal and distal movements of the guide wire 3306 and/or the elongate tube 3307 may be controlled by a user interfacing the proximal end of the catheter 3302. For example, the guide wire 3306 may be coupled to, for example, a guide wire pusher (not shown) which runs the length of the catheter 3302.

The distal end of the guide wire 3306 may be coupled to a capping element 3308 which serves to protective the distal end of the self-expandable stent 3301. The distal end of the elongate tube 3307 may be coupled to an inner anchoring element 3309 which provides additional retrievability of the self-expandable stent 3301.

Outer Anchoring Element

The outer anchoring element 3304 is generally a soft pliable material whose shape may conform to its surroundings such as the wall of catheter 3302 and/or the self-expandable stent 3301) and is able to anchor or otherwise engage the self-expandable stent 3301. The outer anchoring element 3304 may be made from any material that is compatible with one or more embodiments of the subject technology. Preferably, the outer anchoring element 3304 is made from a material that provides some frictional contact between the outer anchoring element 3304 and the self-expandable stent 3301. This frictional contact will primarily be between at least a portion of the inner-facing surface of the outer anchoring element 3304 and the outward-facing surface of the self-expandable stent 3301. This frictional contact provides axial movement control of the self-expandable stent 3301. For example, a distal motion of the outer anchoring element 3304 will cause the self-expandable stent 3301 to be pushed distally towards the target site. Conversely, a proximal motion of the outer anchoring element 3304 will cause the self-expandable stent 3301 to move proximally back into the catheter 3302.

In some embodiments, the proximal motion of the self-expandable stent 3301 and the anchoring element 3304 may also be controlled by a plunger. For example, the plunger may have frictional contact with the anchoring element 3304 which in turn is engaged to a partially deployed self-expandable stent 3301. A retraction of the plunger (i.e., proximal motion) may retract the anchoring element 3304 and the self-expandable stent 3301.

Suitable examples of materials may include, but are not limited to, various thermoplastics, e.g., PTFE, FEP, HDPE, PEEK, etc. In some embodiments, the surface of the outer anchoring element 3304 may have a hydrophilic coating such as PVP or some other plastic coating. Additionally, the surface of the outer anchoring element 3304 may be coated with various combinations of different materials, depending upon the desired results. Optionally, the outer anchoring element 3304 may have additional structural features on its surface which enhance frictional contact between the outer anchoring element 3304 and the self-expandable stent 3301. Suitable examples of structural features may include, but are not limited to, ridges, chevrons, teeth, undulations, and the like.

Figure 3:
FIG. 3 depicts an embodiment of the anchoring element.
Figure 4A:
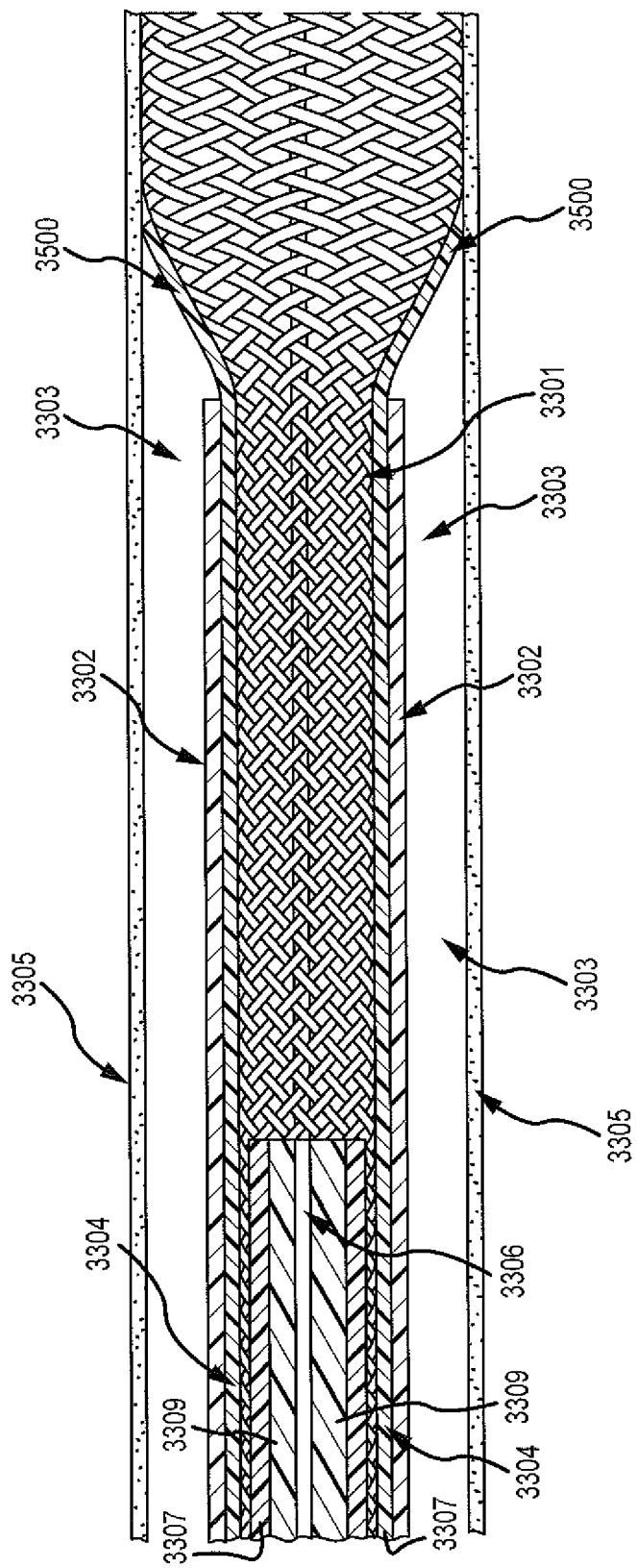
FIGS. 4A and 4B depict embodiments of the resheathable stent delivery system in a partially deployed state.
Figure 4B:
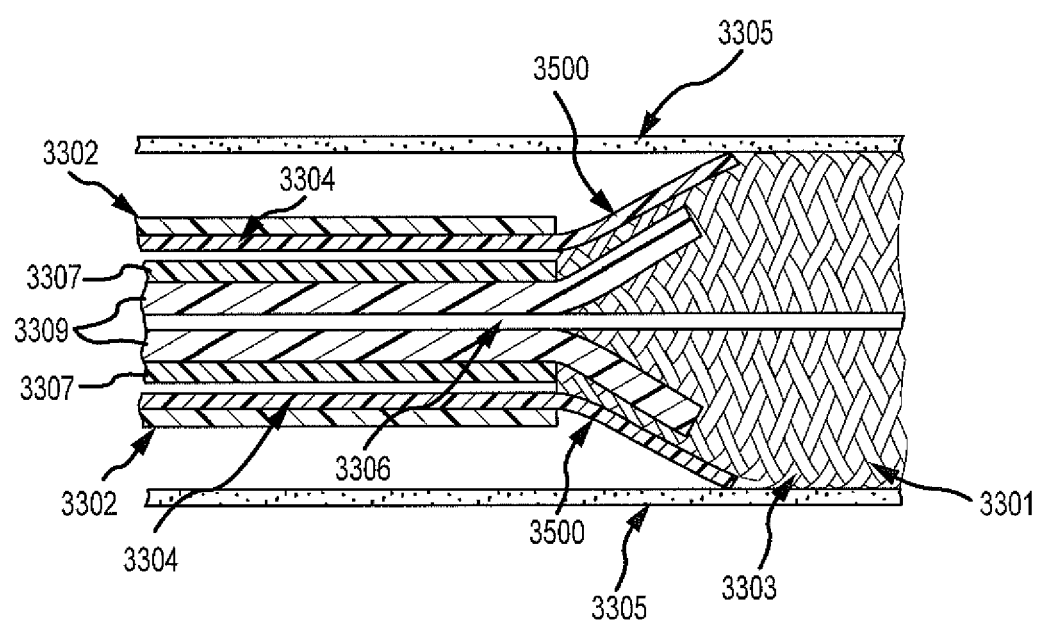

FIG. 3 shows an example of an outer anchoring element 3304 made from a single piece of a thermoplastic material which includes at least one slit (e.g., longitudinal divide) 3400 at the distal end. In the embodiment show in FIG. 3, one side of the outer anchoring element 3304 may have a longer slit while the proximal portion of the outer anchoring element 3304 is primarily intact. This proximal portion provides a tighter fit around the proximal end the self-expandable stent 3301. The slit 3400 allows the distal portion 3500 of the outer anchoring element 3304 to more easily bend or flap out towards the wall of the vasculature 3305 when the distal portion 3500 of the anchoring element and self-expandable stent 3301 is released and/or expanded outside of the catheter (FIG. 4A-4B). In the embodiment shown in FIG. 4A-4B, the distal portion 3500 of the outer anchoring element 3304 has conformed to the expanded portion of the self-expandable stent 3301. In some embodiments, the outer anchoring element 3304 may have a plurality of slits. In other embodiments, the outer anchoring element 3304 may include one or more separate pieces.

Inner Anchoring Element

The inner anchoring element 3309 is generally made from the same materials and may have the same structural features as the outer anchoring element 3304 as described above. In the embodiment shown in FIGS. 2A-2B, the inner anchoring element 3309 is a tube-like piece that has a slit (e.g., longitudinal divide), preferably at its distal end, running at least a portion of the axial length. In some embodiments, the slit may be angled. This slit allows the inner anchoring element 3309 to flare out (similarly to the outer anchoring element 3304) under certain configurations. When the inner anchoring element 3309 has fully flared out, at least a portion of the outward-facing surface of the inner anchoring element 3309 may frictionally engage the inner-facing surface of the self-expandable stent 3301.

As shown in FIGS. 2A-2B, the inner anchoring element 3309 is at least partially encapsulated by the distal end of the elongate tube 3307 which is disposed in the lumen defined by the self-expandable stent 3301. The axial movement of the inner anchoring element 3309 is generally coupled to the axial motion of the elongate tube 3307 which may be controlled at the proximal end of the device. For example, a proximal motion of the elongate tube 3307 causes a relative (to the elongate tube 3307) distal motion of the inner anchoring element 3309. A distal motion of the elongate tube 3307 causes a relative proximal motion of the inner anchoring element 3309. In the preferred embodiment, the inner anchoring element 3309 may be positioned independently of the self-expandable stent 3301 and/or the outer anchoring element 3304.

According to some embodiments, the inner anchoring element 3309 flares radially outward to provide a greater frictional engagement with the stent 3301 when it moves distally relative to stent 3301 than when it moves proximally relative to the stent 3301. For example, the inner anchoring element 3309 may be retracted proximally without substantially engaging the stent 3301, such that the stent 3301 substantially maintains an axial position while the inner anchoring element 3309 retracts proximally. By further example, the inner anchoring element 3309 may be advanced distally while engaging the stent 3301, such that the stent 3301 moves axially with the inner anchoring element 3309.

Capping Element

Referring again to FIGS. 2A-2B, the resheathable stent delivery system 3300 may also include a capping element 3308. In some embodiments shown, the capping element 3308 is attached to the distal end of the guide wire 3306 and engages the distal end of the self-expandable stent 3301. The capping element 3308 may also have a slit (e.g., longitudinal divide), preferably at its proximal end, which allows the capping element 3308 to flare out under certain configurations. One of the advantages of the capping element 3308 is to prevent or reduce the fraying of the distal end of the self-expandable stent 3301. The capping element 3308 is generally made from the same material and may have the same structural features as the outer anchoring element 3304 as described above.

Deployment

While at least some embodiments described herein relate to mechanical detachment of a vascular device using a pusher, any element and/or mechanism that is compatible with one or more embodiments may be used. In many vascular device delivery systems, the detachment of the vascular device from the vascular device delivery system is often an irreversible or difficult to reverse process.

There are typically several distinct stages or states related to the deployment of a stent from the resheathable stent delivery device once the stent is in place near its target site. A user-initiated distal motion of the self-expandable stent 3301 can cause the stent to move towards the target site and eventually deploy. The degree of distal motion will determine whether the stent is partially deployed or fully deployed. Generally, a partially deployed stent will have at least a portion that is not fully expanded. The precise and accurate positioning of a stent is often desired to ensure proper blood flow through blood vessels while restricting blood flow inside the aneurysm.

FIGS. 4A-4B show at least two embodiments of a resheathable stent delivery system in which the self-expandable stent 3301 is in a partially deployed, or expanded, state. In this partially deployed state of the resheathable stent delivery system, the distal end portions of the self-expandable stent 3301 and the outer anchoring element 3304 have moved past the opening at the distal end of catheter 3302. Unconstrained by the catheter 3302, the distal portion of the self-expandable stent 3301 is free to expand and disengage the capping element 3308, which in turn causes the self-expandable stent 3301 to conform to the vasculature wall 3305 of the patient.

As shown in FIGS. 4A-4B, the distal portion of the self-expandable stent 3301 has expanded to the size of the vessel and the surface of the self-expandable stent 3301 is now apposed to the vessel wall 3305. This expansion of the distal portion of the self-expandable stent 3301 also causes the distal portion 3500 of the outer anchoring element 3304 to flare out or otherwise conform to the proximal portion of the expanded self-expandable stent 3301. In this partially deployed state, at least a portion of the proximal portion of the self-expandable stent 3301 is disposed in the catheter 3302 and the distal portion 3500 of the outer anchoring element 3304 frictionally engages at least a portion of the expanded self-expandable stent 3301. As described earlier, this frictional contact is primarily between the inner-facing surface of the distal portion 3500 of the outer anchoring element 3304 and outward-facing surface of the self-expandable stent 3301 and allows the self-expandable stent 3301 to be resheathed when desirable.

Resheathing may take place through any number of means including a distal motion of the catheter 3302 which serves to retract the outer anchoring element 3304 which in turn encapsulates and retrieves the expanded self-expandable stent 3301. This retrieval process causes at least a portion of the expanded self-expandable stent 3301 to return to a compressed state (e.g., FIGS. 2A-2B). The distal motion of the catheter 3302 may be achieved by any number of compatible means. For example, a distal motion of the catheter 3302, a proximal motion of the outer anchoring element 3304, and/or both may resheath the partially deployed self-expandable stent 3301.

FIG. 4A shows an embodiment in which the inner anchoring element 3309 is fully encapsulated in the elongate tube 3307. As described earlier, the elongate tube 3307 may move axially independently of the self-expandable stent 3301 and the guide wire 3306. For example, in the embodiment shown in FIG. 4B, the elongate tube 3307 is positioned near the distal portion 3500 of the outer anchoring element 3304 as the self-expandable stent 3301 begins to expand. Such a configuration would allow both the outer anchoring element 3304 and the inner anchoring element 3309 to engage frictionally the self-expandable stent 3301, thereby ensuring greater retrievability.

Retrieval or resheathing of a partially deployed stent may be accomplished by any number of means depending on the specific configuration of the resheathable stent delivery system. In some embodiments shown in FIG. 4A, the self-expandable stent 3301 may be retrieved, for example, through a distal motion of the catheter 3303 and/or proximal motion of the outer anchoring element 3304. In some embodiments shown in FIG. 4B, the self-expandable stent 3301 may be retrieved, for example, through a distal motion of the catheter 3303 and/or proximal motion of the outer anchoring element 3304 and/or proximal motion of the inner anchoring element 3309, which in turn may be initiated by a proximal motion of the guide wire 3306.

Re-deployment of the self-expandable stent 3301 may be initiated at any point during the retrieval or resheathing process. In some embodiments shown in FIG. 4A, re-deployment may be accomplished, for example, through a proximal motion of the catheter 3303 and/or distal motion of the outer anchoring element 3304 and/or distal motion of the guide wire 3306, which in turn causes the inner anchoring element 3309 to flare out and frictionally engage the inner-facing surface of the self-expandable stent 3301. In some embodiments shown in FIG. 4B, re-deployment may also be accomplished, for example, through a proximal motion of the catheter 3303 and/or distal motion of the outer anchoring element 3304 and/or distal motion of the guide wire 3306, which in turn causes a distal motion of the inner anchoring element 3309.

Figure 5:
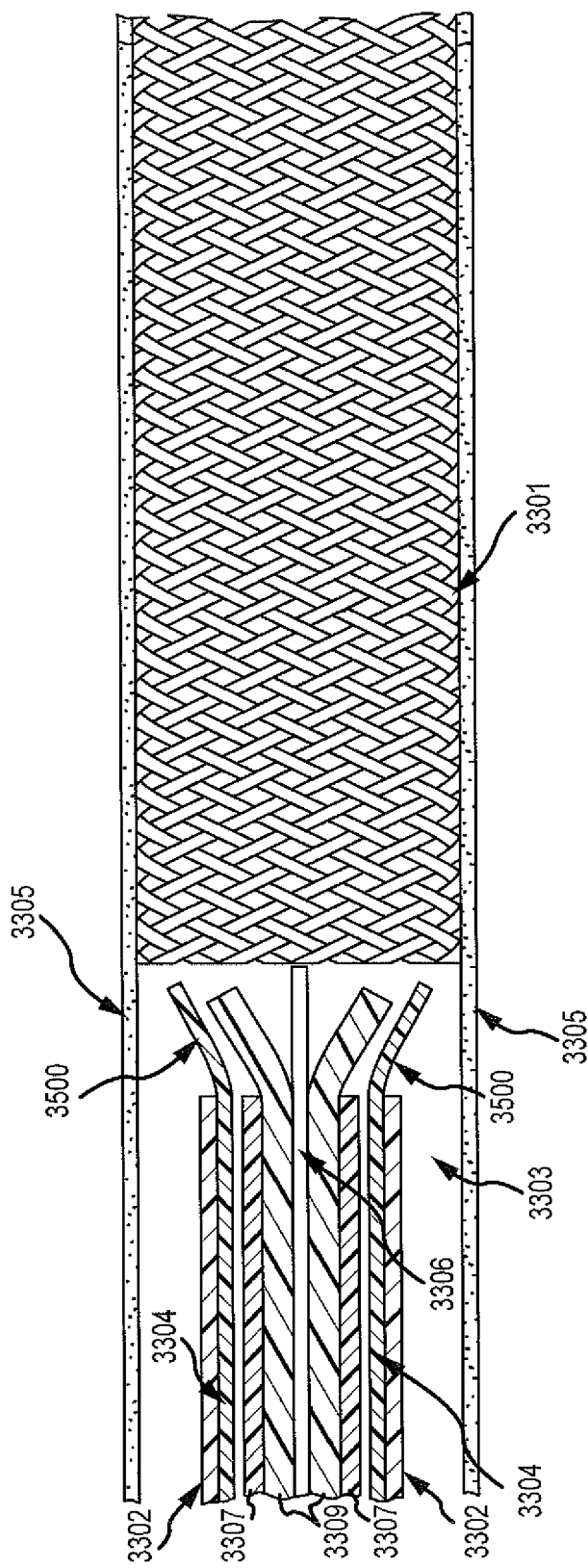
FIG. 5 depicts an embodiment of the resheathable stent delivery system in a fully deployed state.

FIG. 5 shows a resheathable stent delivery system in which a self-expandable stent 3301 is in a fully deployed state. In the fully deployed state of the resheathable stent delivery system 3300, the self-expandable stent 3301 has moved outside of the opening at the distal end of the catheter 3302. The self-expandable stent 3301 is now fully deployed and fully expanded in the vasculature of the patient. As shown in FIG. 5, the outer anchoring element 3304 and the inner anchoring element 3309 are no longer engaged or in contact with the self-expandable stent 3301.

Examples of Particular Lumens

In some embodiments, "occluding device" and "stent" as used herein are used interchangeably. In some embodiments, "cell" and "pore" as used herein are used interchangeably. In some embodiments, porosity refers to a value inversely proportional to lattice density.

The apparatus and methods discussed herein are not limited to the deployment and use of an occluding device within any particular vessels, but may include any number of different types of vessels. For example, in some aspects, vessels may include arteries or veins. In some aspects, the vessels may be suprathoracic vessels (e.g., vessels in the neck or above), intrathoracic vessels (e.g., vessels in the thorax), subthoracic vessels (e.g., vessels in the abdominal area or below), lateral thoracic vessels (e.g., vessels to the sides of the thorax such as vessels in the shoulder area and beyond), or other types of vessels and/or branches thereof.

In some aspects, the suprathoracic vessels may comprise at least one of intracranial vessels, cerebral arteries, and/or any branches thereof. For example, the suprathoracic vessels may comprise at least one of a common carotid artery, an internal carotid artery, an external carotid artery, a middle meningeal artery, superficial temporal arteries, an occipital artery, a lacrimal (ophthalmic) artery, an accessory meningeal artery, an anterior ethmoidal artery, a posterior ethmoidal artery, a maxillary artery, a posterior auricular artery, an ascending pharyngeal artery, a vertebral artery, a left middle meningeal artery, a posterior cerebral artery, a superior cerebellar artery, a basilar artery, a left internal acoustic (labyrinthine) artery, an anterior inferior cerebellar artery, a left ascending pharyngeal artery, a posterior inferior cerebellar artery, a deep cervical artery, a highest intercostal artery, a costocervical trunk, a subclavian artery, a middle cerebral artery, an anterior cerebral artery, an anterior communicating artery, an ophthalmic artery, a posterior communicating artery, a facial artery, a lingual artery, a superior laryngeal artery, a superior thyroid artery, an ascending cervical artery, an inferior thyroid artery, a thyrocervical trunk, an internal thoracic artery, and/or any branches thereof. The suprathoracic vessels may also comprise at least one of a medial orbitofrontal artery, a recurrent artery (of Heubner), medial and lateral lenticulostriate arteries, a lateral orbitofrontal artery, an ascending frontal (candelabra) artery, an anterior choroidal artery, pontine arteries, an internal acoustic (labyrinthine) artery, an anterior spinal artery, a posterior spinal artery, a posterior medial choroidal artery, a posterior lateral choroidal artery, and/or branches thereof. The suprathoracic vessels may also comprise at least one of perforating arteries, a hypothalamic artery, lenticulostriate arteries, a superior hypophyseal artery, an inferior hypophyseal artery, an anterior thalamostriate artery, a posterior thalamostriate artery, and/or branches thereof The suprathoracic vessels may also comprise at least one of a precentral (pre-Rolandic) and central (Rolandic) arteries, anterior and posterior parietal arteries, an angular artery, temporal arteries (anterior, middle and posterior), a paracentral artery, a pericallosal artery, a callosomarginal artery, a frontopolar artery, a precuneal artery, a parietooccipital artery, a calcarine artery, an inferior vermian artery, and/or branches thereof.

In some aspects, the suprathoracic vessels may also comprise at least one of diploic veins, an emissary vein, a cerebral vein, a middle meningeal vein, superficial temporal veins, a frontal diploic vein, an anterior temporal diploic vein, a parietal emissary vein, a posterior temporal diploic vein, an occipital emissary vein, an occipital diploic vein, a mastoid emissary vein, a superior cerebral vein, efferent hypophyseal veins, infundibulum (pituitary stalk) and long hypophyseal portal veins, and/or branches thereof.

The intrathoracic vessels may comprise the aorta or branches thereof. For example, the intrathoracic vessels may comprise at least one of an ascending aorta, a descending aorta, an arch of the aorta, and/or branches thereof. The descending aorta may comprise at least one of a thoracic aorta, an abdominal aorta, and/or any branches thereof. The intrathoracic vessels may also comprise at least one of a subclavian artery, an internal thoracic artery, a pericardiacophrenic artery, a right pulmonary artery, a right coronary artery, a brachiocephalic trunk, a pulmonary trunk, a left pulmonary artery, an anterior interventricular artery, and/or branches thereof. The intrathoracic vessels may also comprise at least one of an inferior thyroid artery, a thyrocervical trunk, a vertebral artery, a right bronchial artery, a superior left bronchial artery, an inferior left bronchial artery, aortic esophageal arteries, and/or branches thereof.

In some aspects, the intrathoracic vessels may also comprise at least one of a right internal jugular vein, a right brachiocephalic vein, a subclavian vein, an internal thoracic vein, a pericardiacophrenic vein, a superior vena cava, a right superior pulmonary vein, a left brachiocephalic vein, a left internal jugular vein, a left superior pulmonary vein, an inferior thyroid vein, an external jugular vein, a vertebral vein, a right highest intercostal vein, a 6th right intercostal vein, an azygos vein, an inferior vena cava, a left highest intercostal vein, an accessory hemiazygos vein, a hemiazygos vein, and/or branches thereof.

In some aspects, the subthoracic vessels may comprise at least one of renal arteries, inferior phrenic arteries, a celiac trunk with common hepatic, left gastric and splenic arteries, superior suprarenal arteries, a middle suprarenal artery, an inferior suprarenal artery, a right renal artery, a subcostal artery, 1st to 4th right lumbar arteries, common iliac arteries, an iliolumbar artery, an internal iliac artery, lateral sacral arteries, an external iliac artery, a testicular (ovarian) artery, an ascending branch of deep circumeclex iliac artery, a superficial circumflex iliac artery, an inferior epigastric artery, a superficial epigastric artery, a femoral artery, a ductus deferens and testicular artery, a superficial external pudendal artery, a deep external pudendal artery, and/or branches thereof. The subthoracic vessels may also comprise at least one of a superior mesenteric artery, a left renal artery, an abdominal aorta, an inferior mesenteric artery, colic arteries, sigmoid arteries, a superior rectal artery, 5th lumbar arteries, a middle sacral artery, a superior gluteal artery, umbilical and superior vesical arteries, an obturator artery, an inferior vesical and artery to ductus deferens, a middle rectal artery, an internal pudendal artery, an inferior gluteal artery, a cremasteric, pubic (obturator anastomotic) branches of inferior epigastric artery, a left colic artery, rectal arteries, and/or branches thereof.

In some aspects, the lateral thoracic vessels may comprise at least one of humeral arteries, a transverse cervical artery, a suprascapular artery, a dorsal scapular artery, and/or branches thereof. The lateral thoracic vessels may also comprise at least one of an anterior circumflex humeral artery, a posterior circumflex humeral artery, a subscapular artery, a circumflex scapular artery, a brachial artery, a thoracodorsal artery, a lateral thoracic artery, an inferior thyroid artery, a thyrocervical trunk, a subclavian artery, a superior thoracic artery, a thoracoacromial artery, and/or branches thereof In some embodiments, a catheter, such as that described in U.S. patent application Ser. No. 12/731,110, which was filed on Mar. 24, 2010 and which incorporated herein by reference in its entirety, can be used to deliver an occluding device delivery system. The delivery system can include an expandable occluding device (e.g., stent) configured to be placed across an aneurysm that is delivered through the distal portion of the catheter, out a distal tip, and into the vasculature adjacent an aneurysm in the middle cerebral artery. A proximal portion of the catheter can remain partially or entirely within a guiding catheter during delivery, and an intermediate portion, taper portion, and distal portion of the catheter can extend distally of the guiding catheter. The occluding device can be released at the target location and can be used to occlude blood flow into the aneurysm. The catheter can be used to reach target locations (e.g., aneurysms) located elsewhere in the body as well, include but not limited to other arteries, branches, and blood vessels such as those described above.

The apparatus and methods discussed herein are not limited to the deployment and use of an occluding device within the vascular system but may include any number of further treatment applications. Other treatment sites may include areas or regions of the body such as organ bodies. Modification of each of the above-described apparatus and methods for carrying out the subject technology, and variations of aspects of the disclosure that are apparent to those of skill in the art are intended to be within the scope of the claims. Furthermore, no element, component or method step is intended to be dedicated to the public regardless of whether the element, component or method step is explicitly recited in the claims.

EXAMPLE 1

This Example describes steps involved in the construction of a resheathable stent delivery system according to one or more embodiments. It will be appreciated that any of steps may be altered and/or appended in any number of ways without departing from the scope of the subject technology.

Figure 6:
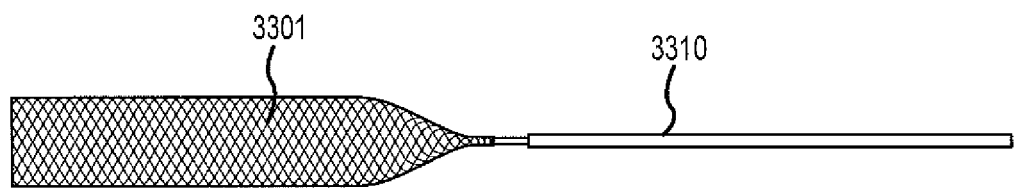
FIG. 6 depicts an exemplary stent as described in Example 1.

In one embodiment, a stent device 3301 was prepared and cut to a desired length (FIG. 6). One end of the stent was lightly squeezed and inserted into an open pin vise which was then locked. Next, a flame from a micro torch was used to make contact with the stent and twisted several times. The stent was released from the vise and flared ends were trimmed off. The twisted cut end (i.e., distal end) the stent was welded to a mandrel 3310 (0.013-0.015 inches).

Figure 7A:
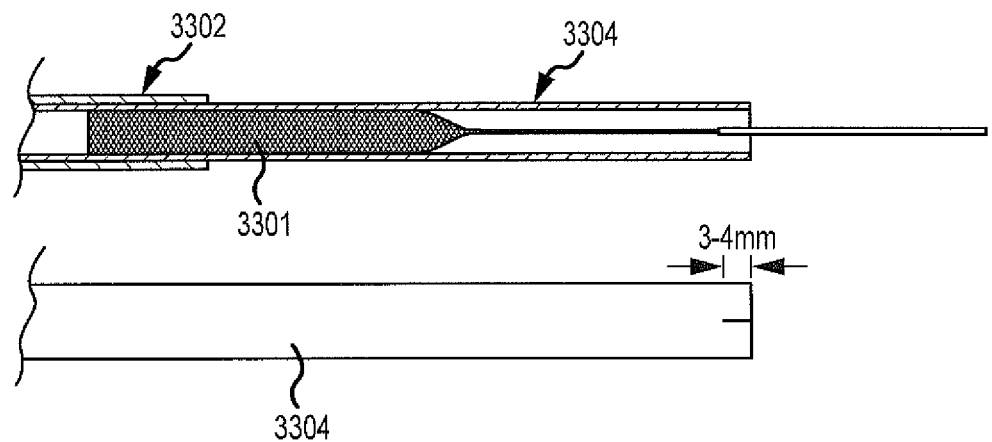
FIG. 7A depicts an exemplary resheathable stent delivery system as described in Example 1.
Figure 7B:
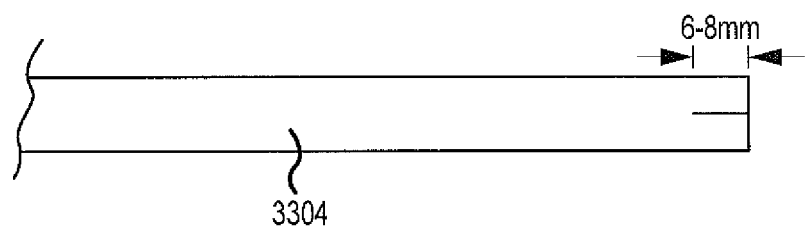
FIG. 7B depicts an exemplary anchoring element as described in Example 1.

The welded mandrel was then inserted through a polyester shrink tubing (anchoring element 3304 or "first tube";

ID=0.023±0.001 inch; wall thickness=0.0010±0.0002 inch). When one end of the mandrel exited from the first tube, the first tube was slit at the distal end in half for about 3-4 mm (FIG. 7A). The slit on only one side of the first tube was extended for another 3-4 mm resulting in a 6-8 mm cut on one side and 3-4 mm cut on the other (FIG. 7B). The first tube was held while the mandrel was pulled until the stent exited the distal end of the first tube. The proximal end of the first tube was then inserted into a laser cut hypotube (stainless steel; ID=0.016 inch; OD=0.020 inch) until the hypotube was abutting the stent device.

Figure 8A:
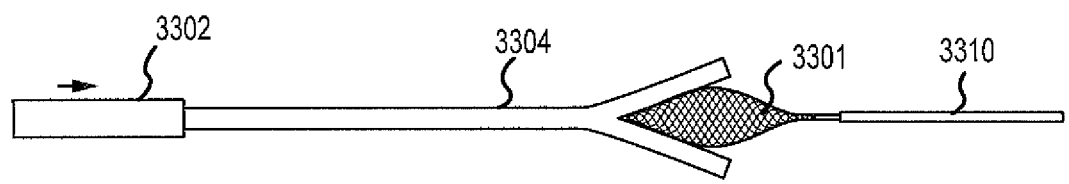
FIG. 8A depicts an exemplary resheathable stent delivery system as described in Example 1.
Figure 8B:
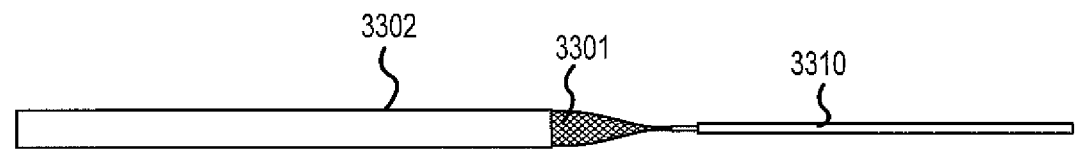
FIG. 8B depict an exemplary resheathable stent delivery system as described in Example 1.
Figure 8C:
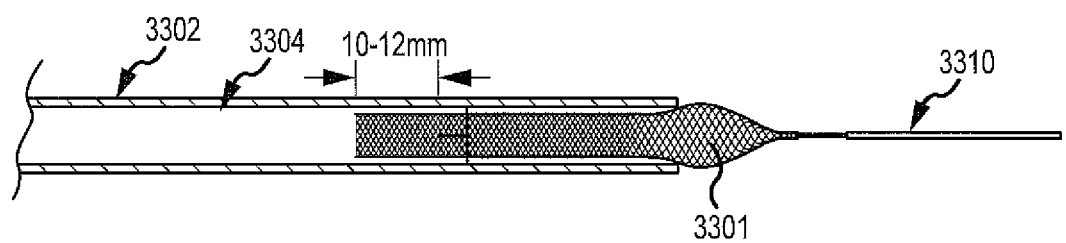
FIG. 8C depicts an exemplary resheathable stent delivery system as described in Example 1.

Next, an introducer sheath 3302 ("outer sheath") slid over the laser cut hypotube/first tube to cover the stent device (FIG. 8A). The mandrel was pulled distally and the introducer sheath was adjusted until the proximal end of the stent device was positioned about 10-12 mm inside the first tube from distal cut line (FIG. 8B-8C).

Figure 9:
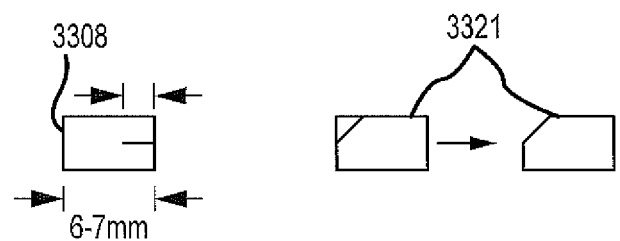
FIG. 9 depicts components of the resheathable stent delivery system as described in Example 1.

A second polyester shrink tubing (capping element 3308 or "second tube"; ID=0.023±0.001 inch; wall thickness 0.0025±0.0001 inch) was cut into two 6-7 mm pieces. The first piece was cut open at one of its ends for 2 mm while the second piece was cut at a slight angle for 1 mm from one end. A polytetrafluoroethylene (PTFE) piece was also heat shrunk to about 1 mm (FIG. 9).

Figure 10A:
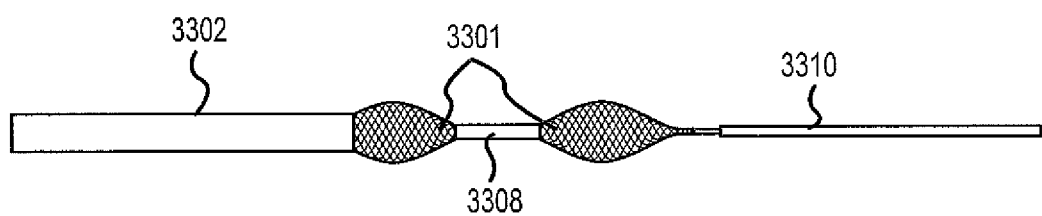
FIG. 10A, 10B, and 10C depict an exemplary resheathable stent delivery system as described in Example 1.
Figure 10B:
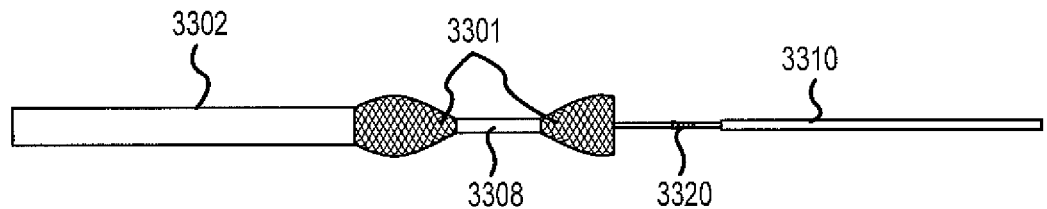

A second polyester shrink tubing 3321 ("third tube") with angled cut slid in over the stent (thereby compressing a portion of the stent) from the distal end of the mandrel (FIG. 10A). The introducer sheath was adjusted if the stent device was not long enough leave a lump on both ends of the second tube. Next, the stent device was cut near the welded area to make it flare or open (FIG. 10B). A proximal guide wire was inserted through via the cut flare stent until the distal tip of the guide wire remained about 5 mm distally outside the first second tube. A 1mm PTFE piece was then shrink over the stent/mandrel transition at 800° F. The first third tube (with 2 mm cut) was slid proximal over the PTFE/guide wire 3320. The resulting distance between the two tubes was about 5-7 mm shorter than the stent length. For example, if the length of the stent to be built or used was 25 mm, the distance between the third tube should be 20 mm or little less.

Figure 10C:
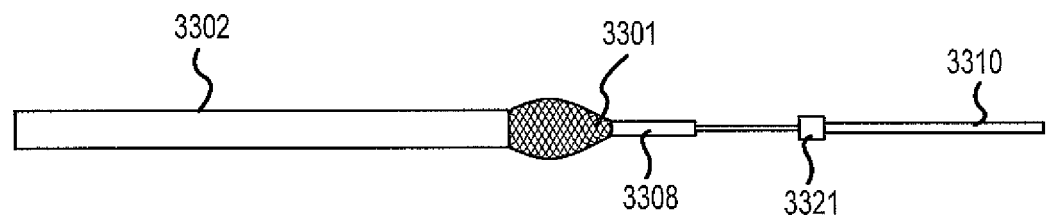
Figure 11:
FIG. 11 depicts an exemplary resheathable stent delivery system as described in Example 1.

A solder station needle was used (~400° F.) to shrink the second polyester shrink tubing to about 2-3 mm. Next, a UV light curing adhesive was applied at the end of shrunk tube to prevent moving (FIG. 10B). The guide wire was pulled back to bring the second tube inside the stent until the third tube was position over the second tube (FIG. 10C). The distance between the polyester shrink tubing pieces should be shorter than the length of the stent (FIG. 11).

Figure 12:
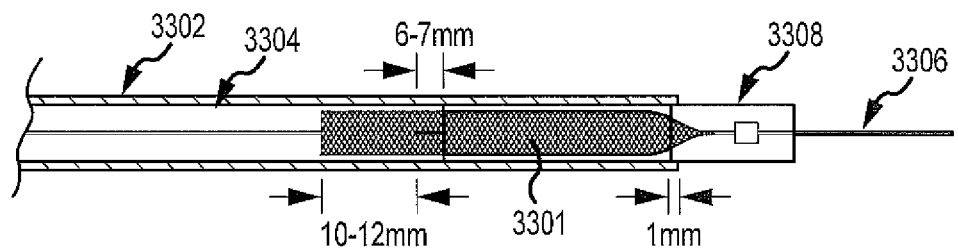
FIG. 12 depicts an exemplary resheathable stent delivery system as described in Example 1.

When the second and third tubes were positioned approximately 1 mm distally of the stent, tweezers were used to grab slightly and push the stent and tubes into the introducer sheath and the stent was maintained distal inside the second tube about 0.5 mm outside the introducer sheath. Tweezers were also used to pull the second tube back until the angle cut end stayed close (~0.1 mm) from the introducer sheath end (FIG. 12).

The guide wire was adjusted as needed to bring the PTFE shrink into the polyester third tube 1 mm away from angle cut line. Using the solder station needle (~400° F.), the third tube was shrunk down from the distal side and over the PTFE shrink. Glue was applied at the end of shrunk third tube and the system was pulled inside the introducer sheath until the end of guide wire completely in and safe. Using a heat gun at 400-430° F., the first tube was shrunk over the introducer sheath starting at about 5 mm from the distal end of laser cut hypotube all the way to the proximal of first tube. The system was loaded then into the coil dispenser.

The foregoing description is provided to enable a person skilled in the art to practice the various configurations described herein. While the subject technology has been particularly described with reference to the various figures and configurations, it should be understood that these are for illustration purposes only and should not be taken as limiting the scope of the subject technology.

There may be many other ways to implement the subject technology. Various functions and elements described herein may be partitioned differently from those shown without departing from the scope of the subject technology. Various modifications to these configurations will be readily apparent to those skilled in the art, and generic principles defined herein may be applied to other configurations. Thus, many changes and modifications may be made to the subject technology, by one having ordinary skill in the art, without departing from the scope of the subject technology.

It is understood that the specific order or hierarchy of steps in the processes disclosed is an illustration of exemplary approaches. Based upon design preferences, it is understood that the specific order or hierarchy of steps in the processes may be rearranged. Some of the steps may be performed simultaneously. The accompanying method claims present elements of the various steps in a sample order, and are not meant to be limited to the specific order or hierarchy presented.

A phrase such as "an aspect" does not imply that such aspect is essential to the subject technology or that such aspect applies to all configurations of the subject technology. A disclosure relating to an aspect may apply to all configurations, or one or more configurations. An aspect may provide one or more examples of the disclosure. A phrase such as "an aspect" may refer to one or more aspects and vice versa. A phrase such as "an embodiment" does not imply that such embodiment is essential to the subject technology or that such embodiment applies to all configurations of the subject technology. A disclosure relating to an embodiment may apply to all embodiments, or one or more embodiments. An embodiment may provide one or more examples of the disclosure. A phrase such "an embodiment" may refer to one or more embodiments and vice versa. A phrase such as "a configuration" does not imply that such configuration is essential to the subject technology or that such configuration applies to all configurations of the subject technology. A disclosure relating to a configuration may apply to all configurations, or one or more configurations. A configuration may provide one or more examples of the disclosure. A phrase such as "a configuration" may refer to one or more configurations and vice versa.

Furthermore, to the extent that the term "include," "have," or the like is used in the description or the claims, such term is intended to be inclusive in a manner similar to the term "comprise" as "comprise" is interpreted when employed as a transitional word in a claim.

The word "exemplary" is used herein to mean "serving as an example, instance, or illustration." Any embodiment described herein as "exemplary" is not necessarily to be construed as preferred or advantageous over other embodiments.

A reference to an element in the singular is not intended to mean "one and only one" unless specifically stated, but rather "one or more." The term "some" refers to one or more. Underlined and/or italicized headings and subheadings are used for convenience only, do not limit the subject technology, and are not referred to in connection with the interpretation of the description of the subject technology. All structural and functional equivalents to the elements of the various configurations described throughout this disclosure that are known or later come to be known to those of ordinary skill in the art are expressly incorporated herein by reference and intended to be encompassed by the subject technology. Moreover, nothing disclosed herein is intended to be dedicated to the public regardless of whether such disclosure is explicitly recited in the above description.

While certain aspects and embodiments of the invention have been described, these have been presented by way of example only, and are not intended to limit the scope of the invention. Indeed, the novel methods and systems described herein may be embodied in a variety of other forms without departing from the spirit thereof. The accompanying claims and their equivalents are intended to cover such forms or modifications as would fall within the scope and spirit of the invention.

What is claimed is:

1. A stent delivery system comprising:
   a deployable stent expandable from a compressed configuration to an expanded configuration, the stent having a proximal end portion and a distal end portion;
   an outer anchoring element having a proximal portion and a distal portion, the outer anchoring element frictionally engaging a radially outer surface of only the proximal end portion of the stent when the outer anchoring element is expanded radially outwardly;
   an inner anchoring element and an elongate tube within the stent, the inner anchoring element comprising a tube structure having a distal end, wherein the inner anchoring element is at least partially slit in half along an axial length of the inner anchoring element, the distal end being movable from a location within the elongate tube to a location distal to the elongate tube and configured to (i) expand radially outwardly and (ii) frictionally engage an inner surface of the stent in the expanded configuration when removed from within the elongate tube; and
   a delivery member configured to encapsulate at least partially the stent and the outer anchoring element prior to expanding the stent, wherein the outer anchoring element is configured to expand radially outwardly when moved distally from within the delivery member.

2. The system of claim 1 further comprising a capping element coupled to a guide wire, the capping element configured to cover at least partially the distal end portion of the stent and the guide wire configured to extend through a lumen of the stent prior to expanding the stent.

3. The system of claim 1, wherein the inner anchoring element is configured to provide greater friction against the inner surface of the stent when the inner anchoring element is advanced distally relative to the stent than when the inner anchoring element is retracted proximally relative to the stent.

4. The system of claim 1, wherein the outer anchoring element frictionally engages the stent when the stent is in the expanded configuration.

5. The system of claim 1, wherein the outer anchoring element is at least partially slit in half along its axial length.

6. The system of claim 1, wherein the proximal end portion of the stent is disposed radially between the elongate tube and the outer anchoring element.

7. The system of claim 1, wherein, when the stent is partially expanded out of the delivery member, (a) the outer anchoring element is configured to frictionally engage the outer surface and (b) the inner anchoring element is configured to frictionally engage the inner surface.

8. A stent delivery system comprising:
   a stent expandable from a compressed configuration to an expanded configuration and having a proximal end portion, a distal end portion, and an inner lumen;
   an outer anchoring element engaging a radially outer surface of only the proximal end portion of the stent when the stent is partially expanded and when the outer anchoring element is expanded radially outwardly, the outer anchoring element having a proximal portion and a distal portion;
   an inner anchoring element comprising a tube structure, wherein the inner anchoring element is at least partially slit in half along an axial length of the inner anchoring element; and
   an elongate tube disposed radially within the stent, the elongate tube configured to at least partially encapsulate the inner anchoring element; and
   a catheter at least partially housing the outer anchoring element and the stent;
   wherein the inner anchoring element has a distal end movable from a location within the elongate tube to a location distal to the elongate tube, the distal end being (i) expandable from a compressed configuration to an expanded configuration when removed from within the elongate tube and (ii) configured to engage an inner surface of the stent,
   wherein the outer anchoring element is movable from a location within the catheter to a location distal to the catheter and is configured to flare radially outwardly when moved distally from within the catheter.

9. The stent delivery system of claim 8, wherein the outer anchoring element frictionally engages the stent in the expanded configuration.

10. The stent delivery system of claim 8, wherein the outer anchoring element is urged to flare radially outward by the stent when the stent is expanded.

11. The stent delivery system of claim 8, wherein the outer anchoring element is at least partially slit in half along its axial length.

12. The stent delivery system of claim 8, wherein the proximal end portion of the stent is disposed radially between the elongate tube and the outer anchoring element.

13. The stent delivery system of claim 8, further comprising a capping element configured to cover at least partially the distal end portion of the stent.

14. The stent delivery system of claim 13, wherein the capping element has a longitudinal divide at a proximal end thereof.

15. The stent delivery system of claim 8, wherein, when the stent is partially expanded out of the catheter, (a) the outer anchoring element is configured to frictionally engage the outer surface and (b) the inner anchoring element is configured to frictionally engage the inner surface.

16. A stent delivery system comprising:
   a deployable stent expandable from a compressed configuration to an expanded configuration, the stent having a proximal end portion and a distal end portion;
   an outer anchoring element having a proximal portion and a distal portion, the outer anchoring element frictionally engaging a radially outer surface of only the proximal and portion of the stent when the outer anchoring element is expanded radially outwardly;
   an inner anchoring element and an elongate tube within the stent, the inner anchoring element having a distal end, the distal end being movable from a location within the elongate tube to a location distal to the elongate tube and configured to (i) expand radially outwardly and (ii) frictionally engage an inner surface of the stent in the expanded configuration when removed from within the elongate tube; and a delivery member configured to encapsulate at least partially the stent and the outer anchoring element prior to expanding the stent, wherein the outer anchoring element is configured to expand radially outwardly when moved distally from within the delivery member, the inner anchoring element comprising a tube structure, wherein the inner anchoring element is at least partially slit in half along an axial length of the inner anchoring element.

17. A stent delivery system comprising:

A stent expandable from a compressed configuration to an expanded configuration and having a proximal end portion, a distal end portion, and an inner lumen;

an outer anchoring element engaging a radially outer surface of only the proximal end portion of the stent when the stent is partially expanded and when the outer anchoring element is expanded radially outwardly, the outer anchoring element having a proximal portion and a distal portion;

an inner anchoring element comprising a tube structure, wherein the inner anchoring element is at least partially slit in halve along an axial length of the inner anchoring element; and an elongate tube disposed radially within the stent, the elongate tube configured to at least partially encapsulate the inner anchoring element; and a catheter at least partially housing the outer anchoring element and the stent;

wherein the inner anchoring element has a distal end movable from a location within the elongate tube to a location distal to the elongate tube, the distal end being (i) expandable from a compressed configuration to an expanded configuration when removed from within the elongate tube and (ii) configured to engage an inner surface of the stent, wherein the outer anchoring element is movable from a location within the catheter to a location distal to the catheter and is configured to flare radially outwardly when moved distally from within the catheter.

* * * * *

UNITED STATES PATENT AND TRADEMARK OFFICE
CERTIFICATE OF CORRECTION

PATENT NO. : 9,724,222 B2  
APPLICATION NO. : 13/553855  
DATED : August 8, 2017  
INVENTOR(S) : Chhuon Lim It is certified that error appears in the above-identified patent and that said Letters Patent is hereby corrected as shown below:

In the Claims

In Column 16, Claim 16, Line 63 should read -- proximal end portion of the stent when the outer In Column 18, Claim 17, Line 3 should read -- slit in half along an axial length of the inner anchoring Signed and Sealed this  
Fourteenth Day of November, 2017

Joseph Matal  
*Performing the Functions and Duties of the*  
*Under Secretary of Commerce for Intellectual Property and*  
*Director of the United States Patent and Trademark Office*